Figure 1:
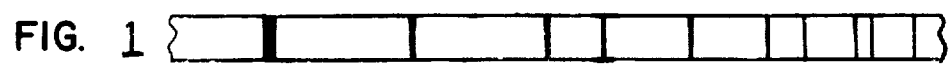

United States Patent [19]

Broecker et al.

[11] 3,954,669

[45] May 4, 1976

[54] PROCESS FOR MAKING AN ETHYNYLATION CATALYST

[75] Inventors: Franz Josef Broecker; Wolfgang Reiss, both of Ludwigshafen; Karl Baer, Weinheim; Siegfried Winderl, Heidelberg-Wieblingen; Wolfgang Schroeder, Bad Durkheim; Herwig Hoffmann, Frankenthal, all of Germany

[73] Assignee: BASF Aktiengesellschaft, Ludwigshafen (Rhine), Germany

[22] Filed: Nov. 19, 1974

[21] Appl. No.: 525,317

[30] Foreign Application Priority Data

Nov. 20, 1973 Germany............................ 2357751

[52] U.S. Cl........................... 252/431 R; 260/635 Y
[51] Int. Cl.²...................... B01J 31/12; B01J 31/14
[58] Field of Search.............. 252/431 R; 260/635 Y

[56] References Cited
UNITED STATES PATENTS 3,650,985   3/1972   Kirchner ......................... 252/431 R

*Primary Examiner*—W. J. Shine
*Attorney, Agent, or Firm*—Johnston, Keil, Thompson & Shurtleff

[57] ABSTRACT

A new catalyst for the manufacture of butynediol from formaldehyde and acetylene, based on a carbonate which contains copper, has the structure of the natural mineral manasseite, also contains magnesium or aluminum or — in place of aluminum — iron or chromium and is converted into the catalyst by reaction of the copper ions with acetylene.

6 Claims, 3 Drawing Figures

PROCESS FOR MAKING AN ETHYNYLATION CATALYST

Since the time of publication of German Pat. No. 725,326, various catalysts have been disclosed for the synthesis of butynediol from formaldehyde and acetylene, known as the Reppe enthynylation reaction. Suitable catalysts have proved to be acetylene compounds of the heavy metals of groups 1 and 2 of the Periodic Table, especially of copper, which can be obtained from acetylene and suitable heavy metal compounds. In a broader sense, the heavy metal compounds are also described as catalysts because of the fact that the actual catalyst, that is to say the acetylide of the heavy metal, is formed directly on passing acetylene into a suitable reaction mixture which contains the heavy metal compound as a "catalyst precursor" and therefore as a rule the manufacture of the catalyst merely entails manufacturing a suitable heavy metal compound. Accordingly, the use of a particular heavy metal compound of this type is regarded as the actual invention in the text which follows.

Copper compounds are known to be particularly suitable heavy metal compounds for the above purpose; they include, say, copper phosphate, copper formate, copper acetate, copper-(II) chloride, copper-(I) chloride, ammoniacal copper sulfate, copper silicate and copper oxide. These compounds can be used unsupported or can first be applied to carriers in the presence of acid-binding additives. The copper is assumed to be in the monovalent state.

In order to suppress the formation of certain by-products (cuprene) during the synthesis of butynediol, additives such as bismuth oxide, bismuth oxyiodide, mercury oxide, mercury iodide, selenium-sulfur, potassium iodide, copper iodide, silver iodide, lead iodide, cerium oxide and selenium dioxide are used (cf. German Pat. No. 740,514 and U.S. Pat. No. 2,300,969).

The addition of activators (described, for example, in British Pat. Nos. 802,792 and 968,928 and German Printed Application No. 1,191,364), such as alkali metal bromides and iodides, alkaline earth metal bromides and iodides, and magnesium silicate, result in only a relatively slight increase in the conversion of formaldehyde.

Catalysts consisting of the above compounds only display a sufficient activity at elevated pressures and temperatures of not less than 90°C; under these conditions, by-products such as propargyl alcohol and methanol are formed, in general in amounts of more than 3%, based on the amount of formaldehyde introduced.

The said catalysts have further disadvantages. In particular, they tend to disintegrate during operation, so that gradually very fine sludges are formed, regardless of whether the catalysts were originally solid bed catalysts or catalyst suspensions. These disintegration products sometimes lead to plant breakdown and require frequent regeneration of the catalyst.

German Printed Application No. 1,804,696 describes a method of converting a particulate copper-(II) compound, preferably basic copper-(II) carbonate, in the form of a suspension in a substantially neutral aqueous medium, into a copper-(I) acetylide complex which is particularly active in the synthesis of butynediol, by treating the suspension simultaneously with formaldehyde and acetylene at a partial pressure of not more than 2.0 bars and at from 50° to 120°C. This catalyst has certain advantages, above all a relatively high activity. However, it is insufficiently stable and insufficiently active specifically for use in processes employing a simple technology.

It is an object of the invention to provide a new ethynylation catalyst, based on a reaction product of acetylene with a basic carbonate containing copper, which combines high activity with high mechnical stability.

We have found that this object is achieved with a catalyst based on a copper-magnesium manasseite, containing copper, magnesium and aluminum, iron-(III) or chromium-(III), of the empirical composition $Cu_m Mg_{6-m} Me(III)_2 (OH)_{16} CO_3$ as the catalyst precursor, said catalyst precursor being transformed into the catalyst by (a) heating to a temperature between 100° and 350°C and (b) reacting said compound after heating both aqueous formaldehyde and acetylene. The catalyst precursor, immediately after synthesis, normally contains 4 moles of water in the above formula.

The catalyst according to the invention is preferentially intended for use as a suspension catalyst.

In the above formula of the manasseite $m$ is a positive number other than zero and less than approximately 4.5, in particular any number between 2 and 4.5. The trivalent metal (Me III) can be aluminum, iron or chromium, but aluminum is preferred.

In general, the catalyst of the invention has a very large internal surface area, of the order of magnitude of 100 m²/g, and has the structure, known from the relevant literature, of natural manasseite $Mg_6Al_2CO_3 \cdot (OH)_{16} \cdot 4 H_2O$, as can be shown by X-ray crystallography. Even without modification by extraneous heavy metals, the catalyst displays high selectivity, can be filtered off easily and has little tendency to form sludges.

Various compounds which have the structure of manasseite have already been produced synthetically; this is described, for example, in British Pat. No. 1,342,020, which is hereby incorporated as a reference.

Accordingly, no claim is made in the present specification for the manufacture of the compounds and for the compounds themselves, where used as catalyst precursors in the present process; further, express reference is made to the above patent with regard to special methods of manufacture and the characterization of these compounds. Example 8 of the said patent describes a catalyst (precursor) suitable for the present invention.

A catalyst according to the invention, based on a manasseite containing copper, magnesium and aluminium, is obtained, for example, as follows:

Water-soluble copper salts, magnesium salts and aluminum salts, for example the nitrates, are precipitated batchwise or continuously, from aqueous solution, with an alkali metal carbonate or bicarbonate solution or a mixture of such a solution with sodium hydroxide solution or potassium hydroxide solution, at a pH of from 7 to 10, preferably 8.2 to 9. The precipitation is preferably carried out in 2 stages. The total concentration of salts in the aqueous solution first mentioned should not exceed 250 g/liter.

The ratios in the salt solution are so chosen that the atomic ratio of the divalent metals (Cu and Mg) to the trivalent metals (Al or Fe and/or Cr) is 3:1; expressed differently, and taking into account the ratio of Cu to Mg, the ratio of the dissolved salts Cu:Mg:Me(III) should be chosen to be m:(6-m):2.

In the most general case, a compound which, according to X-ray crystallography, has the formula

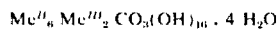

is obtained; depending on the experimental conditions used, this compound can be contaminated with a little basic copper carbonate of the malachite type. In the above formula, the divalent metal Me(II) is a suitable mixture of copper and magnesium whilst the trivalent metal is preferably aluminum.

The precipitation conditions can be chosen to give a product wherein malachite is no longer detectable as a constituent. For this purpose, the temperature is preferably from 70° to 90°C and the precipitation is carried out continuously in two stages, the dissolved mixture of the metal salts being reacted with a solution of alkali metal carbonate and alkali metal hydroxide in a first vessel. Here, the pH is from 7 to 10, preferably from 8.2 to 9.

The amount of carbonate solution preferably corresponds to from 1.1 to 1.3 times the amount theoretically required, whilst the amount of alkali metal hydroxide is chosen in accordance with the requisite pH. Sodium carbonate and NaOH are preferred.

In a second vessel, dilute nitric acid is added to the overflow from the first vessel, to complete the precipitation. To obtain a high proportion of manasseite, it is important that the residence time in the first vessel should be as short as possible. For example, a residence time of from 20 to 25 minutes, calculated from the ratio of the total volume throughput of solution to the effective volume of the precipitation space, should not be exceeded. After the second precipitation process, the precipitate must age for at least 4 hours before filtration. Aging for from 5 to 10 hours is preferred. Of course, longer aging is not disadvantageous from the point of view of achieving a suitable crystal structure but merely uneconomical. A turquoise-colored precipitate is obtained, which can be shown by X-ray crystallography to have the structure of manasseite, and in which malachite is no longer detectable by X-ray crystallography. The precipitate is filtered off, washed and dried.

Since it has been found that a catalyst (precursor) manufactured in this way can still lose substantial amounts of water without losing its specific properties it has been found desirable to subject the dried precipitate to a further treatment in the drying oven, for example at above 100°C, at temperatures rising to 350°C, and then to grind it to a particle size of less than $\mu$.

A catalyst which has been after-treated by heating in this way no longer has the complete structure of manasseite but some characteristic lines of the original X-ray structure diagram remain.

Figure 2:
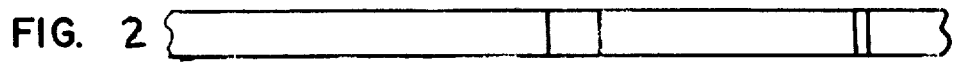

The X-ray diagrams (Guinier camera, $CuK_\alpha$) of manasseite and of the heated product are shown in the drawing as FIGS. 1 and 2, respectively.

Figure 3:

For comparison, the structure of a basic copper carbonate of the malachite type is shown in FIG. 3 of the drawing.

The conversion of the catalyst precursor to the actual catalyst, that is to say to the acetylide compound, is preferably effected according to the following general instructions:

The precursor, which has been comminuted to a particle size of, for example, from 50 to 150$\mu$, and in which larger particles have been sieved out and, if desired, been converted to a usable form by renewed comminution, is suspended in an aqueous formaldehyde solution. The formaldehyde concentration is virtually optional and can be, for example, from 1 to 40 per cent by weight; for example, the catalyst system is very suitable for converting residual formaldehyde contents still present in reaction mixtures where the reaction has already substantially gone to completion.

The suspension obtained is transferred into the reactor. However, it presents no problems to manufacture the suspension in the actual reactor and effect the conversion therein.

The parts of the reactor intended to come into contact with acetylene are next flushed with nitrogen and the reactor containing the suspension is then brought to a temperature of, for example, from 50° to 80°C. Excessively high temperatures should be avoided because by-products may form. Nitrogen can be replaced by acetylene even during the heating-up stage. In the above temperature range, the catalyst is then converted to the acetylide, and the reaction to form butynediol commences. During this period it is desirable to monitor the pH of the solution carefully; the pH should be from 5 to 9 and preferably from 6.5 to 8.

The following should be noted with regard to effecting the ethynylation with the catalyst of the invention:

The catalyst is particularly suitable for processes in which catalyst is suspended in the reaction mixture. Because of its excellent structure, which resists disintegration to a sludge, particularly simple arrangements can be used with this catalyst; for example, the use of a simple tubular reactor provided with one or more perforated plates has proved particularly successful. Using this system, it is possible to remove the reaction mixture from the reaction chamber with the aid of a filter candle without accumulating a filter cake thereon during prolonged operation.

Since the high activity of the catalyst furthermore makes it possible to avoid the use of superatmospheric pressure, an apparatus of remarkable simplicity results.

The amount of catalyst in the suspension depends on the process details and is in general from 1 to 15 per cent by weight, and preferably from 5 to 12 per cent by weight, based on the total amount of reaction mixture. The reaction temperature is from 60° to 110°C and preferably from approximately 65° to 90°C. In general, the total pressure corresponding to the vapor pressure of the solution provides a sufficient reaction pressure, which is normally not greater than 1.5 bars and preferably from 1 to 1.2 bars.

The process can be carried out particularly advantageously in a so-called bubble column, wherein formaldehyde solution and acetylene are introduced from below into a reaction tube of suitable construction which is subdivided into sections by one or more sieve trays or perforated trays and is equipped in the top section with filter candles through which the mixture which has reacted can be withdrawn. In continuous operation it is possible, and in some cases desirable, to arrange several such bubble columns in series to avoid making these units excessively high. Normally, it is desirable that the formaldehyde content in the end product should be as low as possible; since the solubility of acetylene in the solution is relatively low, the feed of reactants to the reactor is as a rule regulated in such a way that a certain excess of acetylene is always present.

MANUFACTURE OF A CATALYST (PRECURSOR) ACCORDING TO THE INVENTION

A stirred kettle cascade consisting of two 10 liter glass flasks with an overflow which limits the contents of each to 6 liters, and equipped with high intensity stirrers, is charged, in the first flask, with 3 liters/hour of a mixture of 14.7 kg of a 14.9 per cent strength copper nitrate solution, 7.35 kg of a 4.9% strength Mg nitrate solution and 10.7 kg of a 4.16 per cent strength Al nitrate solution. The flask has beforehand been filled with 564 g of sodium carbonate and 4.80 g NaHCO$_3$ in 3.9 liters of completely demineralized water and heated to 80°C.

In parallel to the nitrate solution, a mixture of 10 liters of 2M sodium carbonate solution and 20 liters of 4M NaOH solution enters the first flask at a rate of about 19 liters/hour. This rate is regulated so that a pH of 8.6 (measured with a glass electrode) is maintained in the first flask. The precipitation temperature is kept at 80°C. The pH of the solution which overflows into the second flask is adjusted, again continuously and again at 80°C, to 7.8 by adding HNO$_3$ diluted in the ratio of 1:3. The amount of HNO$_3$ added is approximately 5 liters/hour. The precipitation lasts at least 5 hours. The suspension which overflows from the second flask is collected with gentle stirring and before filtration on a filter press is left in the mother liquor for approximately from 4 to 24 hours.

The washed filter cake is then dried for 48 hours at 100°C. Its composition is then:

36.2% of Cu, 6.95% of Mg, 7.05% of Al, 8.2% of CO$_2$ and 0.07% of Na$_2$O and its loss on ignition at 900°C is 30.1%.

The dried powder has a bulk density of 556 g/liter and a porosity of 1.08 cc./g.

Some of the dried filter cake is heated to 350°C for 6 hours. The resulting powder has a bulk density of 413 g/liter and a porosity of 1.23 cc./g.

EXAMPLE 1

For a batchwise experiment, manasseite obtained according to the above description and containing 35% by weight of copper is heated at 300°C for 2 hours. The resulting catalyst (precursor), which contains 45% by weight of copper, is ground and sieved. The fraction of particle diameter less than 100μ is used.

A sufficient amount of this fraction is suspended in an aqueous solution containing 30% by weight of formaldehyde to give a suspension containing 7.4% by weight of the catalyst precursor. 2% by weight of calcium carbonate is then added to this suspension. The batch is now introduced into the nitrogen-flushed reactor. During subsequent heating to 70°C, the nitrogen is replaced by acetylene. The catalyst precursor is converted to the catalyst in the course of half an hour at 70°C. The amount of acetylene fed in through the bottom of the reactor is such that the flow rate, based on the empty reactor and on the actual operating conditions (including the partial pressure of the reaction solution) is 1 cm/second. The total pressure above the reaction solution corresponds to atmospheric pressure. The temperature is then raised to 90°C, the acetylene throughput is doubled and the conversion to butynediol is observed. After 2 hours' reaction time, 94% of the formaldehyde has reacted.

Comparative Experiment

The procedure followed is as in Example 1 except that the same amount of a malachite of the same particle size distribution is used as the catalyst precursor. After 2 hours' reaction time, only 73% of the formaldehyde has reacted.

EXAMPLE 2

The procedure followed is as in Example 1 except that after conversion of the precursor to the catalyst the conversion of the formaldehyde to butynediol is observed at 70°C. After 2 hours' reaction time, 59% of the formaldehyde has reacted.

EXAMPLE 3

The procedure followed is as in Example 1 except that the suspension only contains 3.8% of the catalyst precursor and that the conversion of the formaldehyde to butynediol is observed at 80°C. After 2 hours' reaction time, 55% of the formaldehyde has reacted.

EXAMPLE 4

The above catalyst precursor is used, it is suspended in an aqueous solution containing 30% by weight of formaldehyde to give a suspension containing 9.0% by weight of the catalyst precursor, and 3% by weight of calcium carbonate are added.

The batch of suspension is now fed into the nitrogen-flushed continuously operated reactor. During subsequent heating to 65°C, the amount of acetylene fed in through the bottom of the reactor is increased so that the gas velocity, based on the empty reactor but corrected to operating conditions, including the vapor pressure of the liquid phase, is 4 cm/second. The reaction of formaldehyde and acetylene to give butynediol commences simultaneously with the conversion of the precursor to the catalyst.

30% strength by weight formaldehyde solution is now fed in through the bottom of the reactor in an amount corresponding to an average residence time of 8 hours in the reactor. The reaction product withdrawn continuously from the reactor still contains 8.5% by weight of unconverted formaldehyde and a total amount of less than 1% by weight of by-products detectable by gas chromatography, such as propargyl alcohol and methanol. Retaining the catalyst in the reactor by a filter element presents no difficulties. The formic acid produced from formaldehyde during the reaction is neutralized by occasional addition of sodium bicarbonate solution.

EXAMPLE 5

The procedure followed is as described in Example 4 except that after conversion of the precursor to the catalyst the reaction temperature is set to 75°C and the formaldehyde solution is fed in through the bottom of the reactor in an amount corresponding to an average residence time of 3 hours in the reactor. The reaction product continuously withdrawn from the reactor still contains 10% by weight of unconverted formaldehyde and a total amount of less than 2% by weight of by-products detectable by gas chromatography.

We claim:

1. A process for the manufacture of a catalyst for the production of butynediol from aqueous formaldehyde and acetylene, which comprises a. heating a compound having the crystal structure of the natural mineral manasseite and the empirical formula

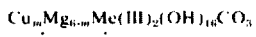

wherein $m$ is a non-zero positive number having a value of up to 4.5 and Me(III) is trivalent Al, Fe or Cr, to a temperature of from 100° to 350°C, and b. thereafter reacting the material with aqueous formaldehyde and acetylene.

2. A process as claimed in claim 1, wherein the material reacted with aqueous formaldehyde and acetylene has been obtained by the following steps:

a.i. forming an aqueous solution of a copper salt, a magnesium salt and an Me(III) salt, said salts being present in the solution in a ratio equivalent to an atomic ratio of Cu:Mg:Me(III) of m:(6-m):2 and in an overall concentration of not more than 250 g/l, Me(III) and m having the meanings given in claim 1, a.ii. precipitating the salts from the solution with an aqueous solution of at least one alkali metal carbonate or bicarbonate at a temperature of from 70° to 90°C and at a pH of from 7 to 10, a.iii. water-washing and drying the precipitate so obtained and a.iv. heating said precipitate to a temperature of from 100° to 350°C.

3. A process as claimed in claim 1, wherein the compound to be heated contains up to 4 moles of water per formula unit.

4. A process as claimed in claim 1, wherein $m$ is from 2 to 4.5 and Me(III) is Al(III).

5. A process as claimed in claim 1, wherein in step (a.ii.) the salts are precipitated with an aqueous solution of alkali metal carbonate and alkali metal hydroxide, the amount of carbonate solution used being from 1.1 to 1.3 times the theoretical amount required for complete precipitation and the alkali metal hydroxide being present in an amount to provide a pH during precipitation of from 8.2 to 9.

6. A catalyst produced by the process of claim 1.

* * * * *